United States Patent [19]

Kuc et al.

[11] Patent Number: 5,594,849
[45] Date of Patent: Jan. 14, 1997

[54] BIOMEDICAL MAGNETISM IMAGING APPARATUS AND METHOD

[75] Inventors: Roman B. Kuc; James J. Szinger, both of New Haven, Conn.; Takehiko Hayashi, Kawasaki, Japan; Takao Goto, Kawasaki, Japan; Yoshiyasu Nakashima, Kawasaki, Japan; Takaki Shimura, Kawasaki, Japan; Kenji Kawabe, Kawasaki, Japan

[73] Assignees: Yale University, New Haven, Conn.; Fujitsu Limited, Kawasaki, Japan

[21] Appl. No.: 743,065

[22] Filed: Aug. 9, 1991

[51] Int. Cl.$^6$ ............................................. G06K 15/00
[52] U.S. Cl. .................. 395/135; 128/653.1; 364/413.22
[58] Field of Search .................. 364/413.13, 413.14, 364/413.15, 413.16, 413.18, 413.19, 413.22; 324/248; 128/653.1, 732, 731, 653.2; 345/132, 129, 127, 173; 382/6, 47; 395/128, 139, 135

[56] References Cited

U.S. PATENT DOCUMENTS

| | | | |
|---|---|---|---|
| 4,598,368 | 7/1986 | Umemura | 364/414 |
| 4,928,253 | 5/1990 | Yamauchi et al. | 395/139 |
| 5,046,027 | 9/1991 | Taaffe et al. | 395/133 |
| 5,063,348 | 11/1991 | Kuhara et al. | 324/307 |
| 5,285,385 | 2/1994 | Igarashi et al. | 364/413.13 |
| 5,291,889 | 3/1994 | Kenet et al. | 364/413.13 |

FOREIGN PATENT DOCUMENTS

| | | |
|---|---|---|
| 3725532A1 | 2/1989 | Germany. |
| 3922150A1 | 1/1991 | Germany. |

OTHER PUBLICATIONS

Okada, et al, "Society for Neuroscience Abstracts–509.16"; Current Density Imaging as a Method of Visualizing Neuronal Activity 1990.

Okada, et al; "Current Density Imaging as a Method of Visualizing Neuronal Activity of the Brain"; 1990; p. 1241.

Jeffs, et al; "An Evaluation of Methods for Neuromagnetic Image Reconstruction"; 1987; pp. 713–723.

Smith, et al; "Linear Estimation Theory Applied to the Reconstruction of a 3–D Vector Current Distribution"; (1990) pp. 658–667.

Abraham–Fuchs, et al., "MCG Inverse Solution: Influence of Coil Size, Grid Size, Number of Coils, and SNR", *IEEE Transactions on Biomedical Engineering*, vol. 35, No. 8, Aug. 1988, pp. 573–576.

Knuutila et al., "On the Spatial Locating Accuracy of Multichannel Magnetometers", *Advances in Biomagnetism*, pp. 713–716, 1989.

Paulson et al., "Experimental Accuracy of Localization of Current Dipoles in a Spherical Phantom", *Advances in Biomagnetism*, pp. 717–720.

Society for Neuroscience Abstracts, vol. 16, 1990, p. 1241.
Society for Neuroscience Abstracts, 509.16, "Current Density Imaging as a Method of Visualizing Neuronal Activity of the Brain", by Okada et al., (1990), p. 1241.

(List continued on next page.)

*Primary Examiner*—Jack B. Harvey
*Assistant Examiner*—X. Chung-Trans
*Attorney, Agent, or Firm*—Staas & Halsey

[57] ABSTRACT

A method and apparatus for performing biomagnetic imaging to determine the location and intensity of current sources within a subject includes a sensor unit for sensing the magnetic field within the subject and for providing sensing signals. A signal processor defines a grid having multiple grid points and performs inverse estimation to determine the distribution of current sources on the defined grid based on the sensing signals. The signal processor then modifies the grid to improve the resolution of the current sources distributed on the grid. A control unit controls the operation of the signal processor and processes image data to provide magnified and non-magnified displays on a display unit. The biomagnetic imaging method and apparatus can be combined with a system for providing magnetic resonance imaging data so as to produce a superimposed display including an MRI image and a biomagnetic image.

4 Claims, 16 Drawing Sheets

OTHER PUBLICATIONS

SPIE, vol. 767, Medical Imaging (1987), "Bioelectric Current Image Reconstruction from Measurement of the Generated Magnetic Fields", by Dallas et al., pp. 2–9.

IEEE Transactions on Biomedical Engineering, vol. BME–32, No. 11, Nov. 1985, "A Comparison of Moving Dipole Inverse Solutions Using EEG's and MEG's", by Cuffin, pp. 905–910.

IEEE Transactions on Biomedical Engineering, vol. BME–34, No. 9, Sep. 1987, "An Evaluation of Methods for Neuromagnetic Image Reconstruction", by Jeffs et al., pp. 713–723.

Phys. Med. Bio, 32, (1989), "Basic Mathematical and Electro–magnetic Concepts of the Biomagnetic Inverse Problem", by Sarvas, pp. 11–22.

Applied Optics, vol. 29, No. 5, Feb. 10, 1990, "Linear Estimation Theory Applied to the Reconstruction of a 3–D Vector Current Distribution", by Smith et al., pp. 658–667.

Journal of the Optical Society of America, vol. 54, No. 7, Jul. 1964, "Diffraction and Resolving Power" by Harris, pp. 931–936.

Numer. Math., Bd. 14, Handbook Series Linear Algebra, (1970), "Singular Value Decomposition and Least Squares Solution", by Golub et al., pp. 403–420.

IEEE Transactions on Acoustics, Speech, and Signal Processing, vol. ASSP–29, No. 4, Aug. 1981, "SVD Pseudoinversion Image Reconstruction", by Shim et al., pp. 904–909.

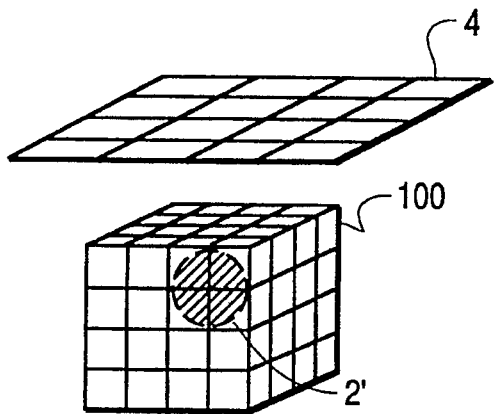
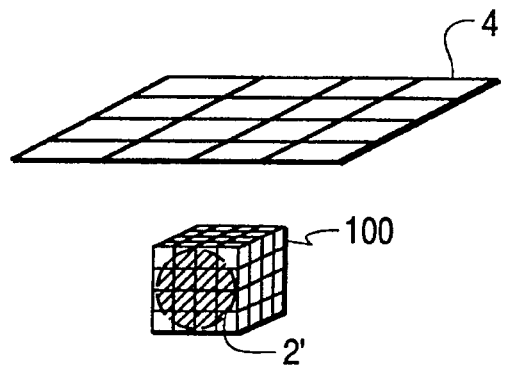
FIG. 9(a)          FIG. 9(b)
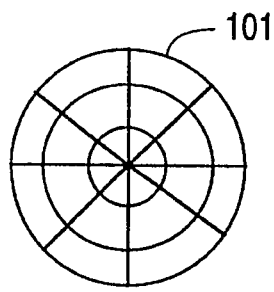
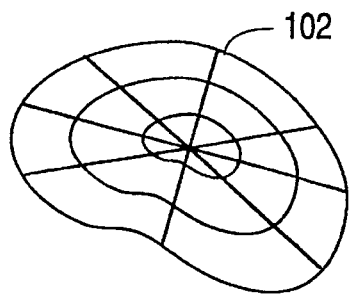
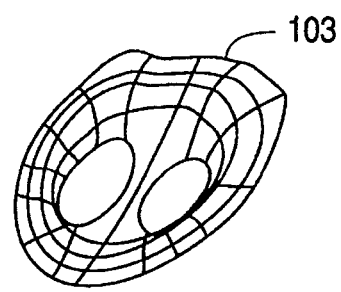
FIG. 10(a)     FIG. 10(b)     FIG. 10(c)

BIOMEDICAL MAGNETISM IMAGING APPARATUS AND METHOD

BACKGROUND OF THE INVENTION

1. Field of the Invention

The present invention relates to an imaging apparatus and method for displaying magnified images of sequentially estimated areas of current sources for estimating the position of an active area within a living body by using a biomedical magnetism measuring apparatus, including a highly sensitive magnetic field sensor, for example, a SQUID (Superconducting QUantum Interference Device) for measuring a magnetic field generated from a living body.

2. Description of the Related Art

With recent advances in superconductive device technology, highly sensitive biomedical magnetism measuring apparatus utilizing a SQUID have recently been employed in medical diagnostic apparatus. Such apparatus, which are also referred to as biomagnetometers, SQUID computed tomography (SQUID CT), magnetic source imaging (MSI), biomagnetic imaging (BMI), magnetoencephalograms (MEG), and magnetocardiograms (MEG) operate as follows. Electric sources within a living body simultaneously generate a low level magnetic field. Therefore, performing an inverse estimation (or inverse problem) of the active area within a living body by measuring the distribution of this magnetic field is expected to be useful for diagnosis of diseased regions within a living body. The terms inverse estimation and inverse problem refer to an algorithm in which a measured magnetic field is employed for estimating the location and/or distribution of the electric sources within the body. The position of a current source which acts as a magnetic field generating source is estimated to analyze heart disease and brain function disease from the measured magnetic field. For this purpose, a current dipole is used as a model of a biological source and is estimated within a homogeneous conductor using a computation model. A current dipole is a short segment of current which is used to illustrate a transient current flow in a small area. The inverse problem approach is employed for determining the current distribution for which the computed magnetic field becomes equal to the measured magnetic field. In accordance with the inverse problem approach, an algorithm is used to move the estimated value of the current dipole to the position for which the corresponding computed magnetic field approximates the measured magnetic field. The algorithm which is employed is based on the least square error solution (see Equation (5) below).

The above-described biomagnetic measuring apparatus should not be confused with magnetic resonance imaging (MRI) which detects only the configuration of a structure. Instead, the subject invention is directed to determining the functional state of an organ by detecting current paths in the body and particularly the brain (so-called neuromagnetism) and the heart (so-called cardiomagnetism). To indicate the magnitude of the magnetic fields created by such current flow in a living body, the neuromagnetic field is approximately $10^{-14}$ tesla, while the cardiomagnetic field is $10^{-12}$ tesla. The magnetic field is measured in order to determine the current amplitude and position of the equivalent current dipole.

Biomagnetometers are currently available in the art. For example, Biotechnology Incorporated (BTi) produces a neuromagnetometer utilizing a SQUID. Other biomagnetometers are manufactured by Siemens and CTF of Canada.

Referring to FIG. 18, in prior art biomedical magnetism measuring apparatus, a homogeneous semi-infinite conductor model of the torso, for example, is used for estimation of the current source in the heart (S1). Alternatively, a homogeneous or multilayer concentric conductor sphere can be used as a model for the head. The parameters of the current dipoles for the heart model are then estimated (S2) and the magnetic field $B_c$ based on these estimated dipoles is calculated (S3). The magnetic field of the heart in the living body is measured (S4) and the measured data $B_m$ is input to the computer (S5). A current dipole which minimizes an objective function equal to the squared difference between the measured magnetic field and the computed magnetic field, has been considered as the estimated position of the current source (also referred to above as the inverse problem or inverse estimation). Therefore, the measured value $B_m$ and the computed value $B_c$ are compared (S6) and if the squared error is minimized (S7) then the distribution of the current dipoles is displayed (S8). If the error is large (S7) then the parameters of the test dipoles are modified (S9) and the magnetic field $B_c$ is recalculated based on the newly set dipoles (S3).

The above-described approach for determining the amplitudes and positions of current dipoles is used in a number of different fields including the above-described biomedical magnetism apparatus and in other fields where the determination of current dipoles is desirable. However, certain problems are inherent in this approach. Local minima in the squared error between the measured and computed magnetic fields, can produce incorrect solutions to the dipole parameters. To overcome this problem, a long time has been required to obtain accurate current source localization because the computation does not converge within a finite amount of time to the correct solution (i.e., the global minimum of the objective function in the inverse problem).

As explained above, the least square error method for solving such a non-linear system requires repeated computation. As a method of avoiding such repeated computation, it has been suggested to fix the position of current dipoles on grid points, thereby making the problem linear. Such methods are described in, for example, Jeffs et al., "An Evaluation of Methods for Neuromagnetic Image Reconstruction", IEEE Transactions on Biomedical Engineering, Vol. BME-34, No. 9, September 1987, pp. 713–723; Smith et al., "Linear Estimation Theory Applied to the Reconstruction of a 3-D Vector Current Distribution", Applied Optics, Vol. 29, No. 5 (1990), pp. 658–667; and Sarvas, "Basic Mathematical and Electromagnetic Concepts of the Biomagnetic Inverse Problem", 1989, Phys. Med. Biol. 32, pp. 11–22, the contents of all which are incorporated by reference. A method for obtaining a least square solution by relating the measured magnetic field to the intensity of the current dipole by using simultaneous linear equations can be then formulated. To express the measured magnetic field obtained by pickup coils and the amplitude of the current dipole on each grid point with simultaneous linear equations, the distribution of the current dipoles is defined on a set of fixed grid points. The amplitudes in three directions of n current dipoles are defined as $(q_{1x}, q_{1y}, q_{1z}) \ldots (q_{nx}, q_{ny}, q_{nz})$; the positions of the corresponding grid points are defined as $(x_1', y_1', z_1') (x_n', y_n', z_n')$; the amplitudes in three directions of the magnetic field measured by m pickup coils at m points are defined as $(b_{1x}, b_{1y}, b_{1z}) \ldots (b_{mx}, b_{my}, b_{mz})$; the positions of the corresponding pickup coils are defined as $(x_z, y_1, z_1) \ldots (x_m, y_m, z_m)$, the current dipole vector $Q=\{q_1, q_2, \ldots q_n\}^T$ and the measured magnetic field vector $B_m=(b_1, b_2, \ldots b_m)^T$. Based on the Biot-Savart law, the simultaneous linear equation B=AQ can be solved, where the matrix of coefficients A is given by:

$$A = \begin{vmatrix} a_{11} & a_{12} & . & . & a_{1n} \\ a_{21} & a_{22} & . & . & a_{2n} \\ . & . & . & . & . \\ . & . & . & . & . \\ a_{m1} & a_{m2} & . & . & a_{mn} \end{vmatrix} \quad (1)$$

Moreover, the elements of the equation $B_m=AQ$ can be expressed as follows:

$$\begin{vmatrix} b_1 \\ b_2 \\ . \\ . \\ b_m \end{vmatrix} = \begin{vmatrix} a_{11} & a_{12} & . & . & a_{1n} \\ a_{21} & a_{22} & . & . & a_{2n} \\ . & . & . & . & . \\ . & . & . & . & . \\ a_{m1} & a_{m2} & . & . & a_{mn} \end{vmatrix} \begin{vmatrix} q_1 \\ q_2 \\ . \\ . \\ q_n \end{vmatrix} \quad (2)$$

Here, from the Biot-Savart law, elements of each coefficient matrix can be obtained from the following expression:

$$a_{ij} = \frac{\mu_0}{4\pi\{(x_i-x_j')^2+(y_i-y_j')^2+(z_i-z_j')^2\}^{3/2}} \times \begin{vmatrix} 0 & z_i-z_j' & -(y_i-y_j') \\ -(z_i-z_j') & 0 & x_i-x_j \\ y_i-y_j & -(x_i-x_j') & 0 \end{vmatrix} \quad (3)$$

The equation $B_m=AQ$ is a linear equation which is determined by the current dipole positions and pickup coil positions. Therefore, the current dipole values Q can be obtained by solving this equation when m, the number of measurements, equals n, the number of unknowns. If the coefficient matrix A is a non-singular matrix, the inverse matrix $A^{-1}$ exists and a current dipole distribution Q can be solved directly from $$Q=A^{-1}B_m \quad (4)$$

However, if the coefficient matrix A is singular or if n>m, the inverse matrix cannot be obtained and a unique solution does not exist. However, in this case, the product $A^TA$ of the coefficient matrix A and transposed matrix $A^T$ becomes a square matrix and $A^TA$ can be inverted when the column vectors of A are independent. In this case, the least squares solution, denoted $\hat{Q}_c$, which minimizes $$\sum_{i=1}^{m} (b_i-b_{c,i}(\beta))^2 \quad (5)$$

which is the squared sum of the differences of measured values $B_m$ and computed values $B_c=A\hat{Q}_c$, given by the normal equation $$\hat{Q}_c=(A^TA)^{-1}A^TB_m \quad (6)$$

can be obtained as described by Strang, "Linear Algebra and Its Applications", 1980, New York; ACADEMIC PRESS, INC., the contents of which is incorporated by reference. Under the least square error method of Equation (5), the parameter $\beta$ defines the test dipole position x', y' and z' and dipole strength $q_x$, $q_y$ and $q_z$. Equation (6) refers to the formulation which is one case of the least square error solution using singular value decomposition. Thus, the terms inverse estimation and inverse problem used above are based on the least square solution of Equation (5).

Moreover, when the matrix A is singular, where the column vectors of matrix A are not independent (i.e., rank (A)<n), the inverse matrix of $A^TA$ does not exist and therefore a unique solution cannot be obtained. In this case, singular value decomposition can be utilized.

In accordance with singular value decomposition, a desired (m×n) matrix A can be decomposed to $$A=U\Lambda V^T \quad (7)$$

with the m×m orthogonal matrix U, m×n diagonal matrix $\Lambda$ and (n×n) orthogonal matrix V. $\Lambda$ is a diagonal matrix where the elements or singular values $\lambda_i$ (i=1, 2 . . . m) are the square roots of the eigenvalues of $AA^T$ and $A^TA$ which are arranged on the diagonal in descending order and U and V are eigenvectors of $AA^T$ and $A^TA$, respectively, as described in Forsythe et al., "Computer Methods for Mathematical Computations, Prentice-Hall, New Jersey, (1978), the contents of which are incorporated by reference.

In this case, the least-square minimum-norm solution $\hat{Q}^+$ of Equation (4) above can be obtained from the following equation for the generalized inverse matrix $$\hat{Q}^+=V\Lambda^+U^TB_m=A^+B_m \quad (8)$$

Here, $\Lambda^+$ is a diagonal matrix whose element is $$\lambda^+_i=1/\lambda_i \quad (9)$$

when $\lambda_i$ is not equal to zero, $\lambda^+_i=0$ when $\lambda_i=0$. $A^+$ is a pseudo inverse matrix, where the inverse matrix $A^{-1}$ is extended to an arbitrary (m×n) matrix from an (n×n) square matrix.

A generalized inverse matrix method utilizing normal equations and a method utilizing singular value decomposition are effective for obtaining the density distribution of many current dipoles because a multi-dipole model is assumed. In this case, once the inverse matrix is obtained by using the normal equations or singular value decomposition, the current source density distribution Q can be obtained simply by multiplying the measured values $B_m$ either by the coefficient $A^+$ as in Equation (8) or by $(A^TA)^{-1}A^T$ as in Equation (6). The distribution of current dipoles can then be obtained with higher speed than with the iterative method for solving the nonlinear least square system in which the position is estimated by moving current dipoles.

In the technique for expressing the relationship between magnetic field intensity and current dipole locations with simultaneous linear equations and obtaining a generalized inverse matrix from the normal equations, a method for dividing the higher current dipole intensity area based on the initial estimated value is known, and is described in Okada a al., "Current Density Imaging as a Method of Visualizing Neuronal Activity of the Brain", Society for Neuroscience Abstracts, 509.16:1241 (1990), the contents of which is incorporated by reference. However, in this method, current dipole resolution can be improved while leaving grid points existing in the peripheral area, but since the number of grid points of current dipole locations increases through division into subsections, the influence of the limited number of pickup coils limits the resolution. In addition, Okada's method assumes a current dipole plane (source plane) which is parallel to the measurement plane and does not describe a flexible grid point distribution method and a display method therefor.

As described above, the number of sensors m must be equal to or larger than the number of current dipoles n in order to accurately obtain the intensity distribution of current dipoles from the least square solution of such simultaneous linear equations. Therefore, a large number of pickup coils and SQUID magnetometers for measuring magnetic field intensity are required for estimating the position of current dipoles with an accuracy of several millimeters required for medical diagnosis. It has also been impossible to realize a real-time apparatus for displaying movement of dipole sources.

SUMMARY OF THE INVENTION

It is an object of the present invention to provide a biomedical magnetism imaging method and apparatus for displaying a desirably magnified image of the distribution of current sources having high resolution by using a comparatively smaller number of pickup coils than is needed for an equivalent resolution over the entire region of interest.

It is a further object of the present invention to provide a biomedical magnetism imaging apparatus which obtains the distribution of current sources by solving the least square solution of simultaneous linear equations using the normal equations and singular value decomposition as the methods of estimating current sources.

It is a still further object of the present invention to provide a method and apparatus for displaying medical imaging data including MRI data and biomagnetic imaging data (BMI or MSI data).

The method and apparatus of the present invention provide a number of advantages over the prior art. In particular, currently available biomagnetic imaging apparatus are only capable of displaying a single dipole. While multiple dipoles have been discussed, it has been thought that multiple dipole display arrangements would require many pickup coils in order to achieve acceptable resolution. The present invention overcomes these deficiencies by providing a biomagnetic imaging method and apparatus which is capable of displaying a desirably magnified image of multiple dipoles, while using a relatively small number of pickup coils.

These together with other objects and advantages will become apparent from the following description of the preferred embodiments in conjunction with the accompanying drawings, wherein like reference numerals refer to like parts throughout.

BRIEF DESCRIPTION OF THE DRAWINGS

FIGS. 9(a) and 9(b) are diagrams for illustrating the use of a three-dimensional grid in accordance with the present invention;

FIGS. 10(a), 10(b) and 10(c) are diagrams for illustrating the use of a polar coordinate grid, a brain-shaped grid and a heart-shaped grid in accordance with the present invention;

DESCRIPTION OF THE PREFERRED EMBODIMENTS

Figure 1A:
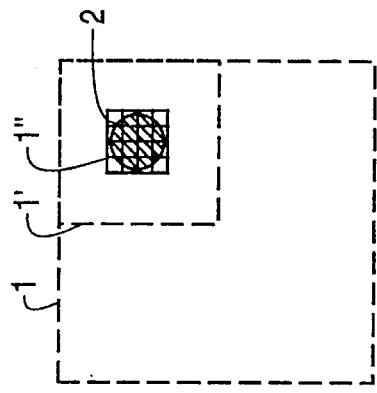
FIGS. 1(a), 1(b) and 1(c) are diagrams for explaining the principle of the present invention in which a current dipole grid for a particular current source distribution is successively reduced in size.
Figure 1B:
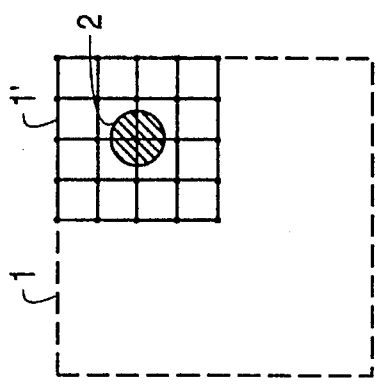
Figure 1C:
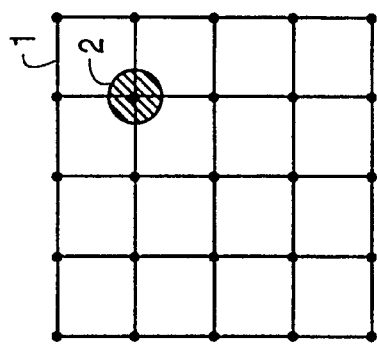

In the present invention, an estimated current dipole grid 1 is first roughly or coarsely set to enclose the entire region in which it is probable that one or more current dipoles 2 exist, as shown in FIG. 1(a). A generalized pseudo inverse matrix $A^+$ is obtained by the normal equations or singular value decomposition of Equations (6) and (8), and reconstruction of current dipole $\hat{Q}_c$ is carried out by multiplying such matrix with the measured magnetic field $B_m$ for the initial estimation of the distribution of current sources. Next, as shown in FIG. 1(b) the estimated current dipole grid 1 is reduced to produce a reduced estimated current dipole grid 1' which includes the active region of reconstructed current sources or dipoles 2 for the purpose of improved current dipole position estimation. And, as illustrated in FIG. 1(c), the reduced estimated current dipole grid 1' is further reduced to produce a twice reduced estimated current dipole grid 1' which includes the active region of reconstructed current sources. This further improves the current dipole position estimation accuracy.

As explained above, inverse estimation with higher resolution can be realized with a smaller number of pickup coils by gradually reducing the estimated current dipole grid 1 to always include the active area of the current source, while the number of points of potential current dipoles (grid points) is kept constant. That is, the number of grid points per unit area is increased, thereby improving resolution. The dipole grid can be reduced as many times as necessary to achieve a desired resolution.

Figure 2:
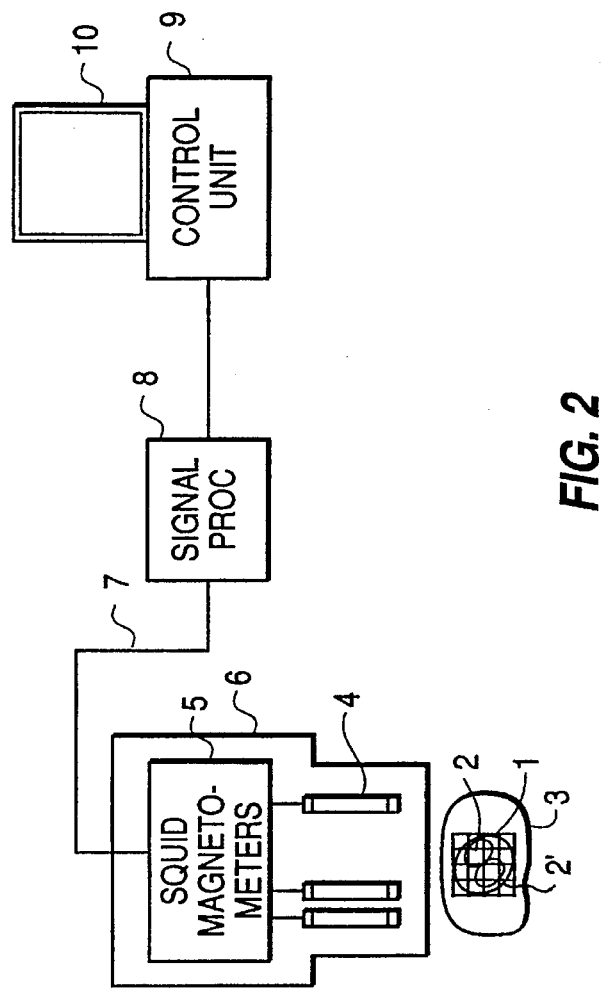
FIG. 2 is a schematic diagram of an embodiment of the present invention.

FIG. 2 is a schematic diagram of a preferred embodiment of the present invention, illustrating a biomedical magnetism measuring apparatus for estimating the position of current sources or dipoles 2 within an area of electrical activity 2' based on the measured magnetic field of the heart or other current producing source. In accordance with the invention, a magnetic field generated by current sources in a living body 3 is sensed by pickup coils 4 which generate magnetic signals which are then converted to proportional electrical signals or sensing signals 7 by SQUID magnetometers 5. The pickup coils 4 and SQUID magnetometers 5 together form a sensing unit 6. The proportional electrical signals 7 output by the SQUID magnetometers 5 are processed by a signal processor 8 which processes the proportional electrical signals 7 by performing the inverse estimation and produces display data as an output. A control unit 9 receives the display data and provides an output signal which is used to drive a display 10.

Figure 3:
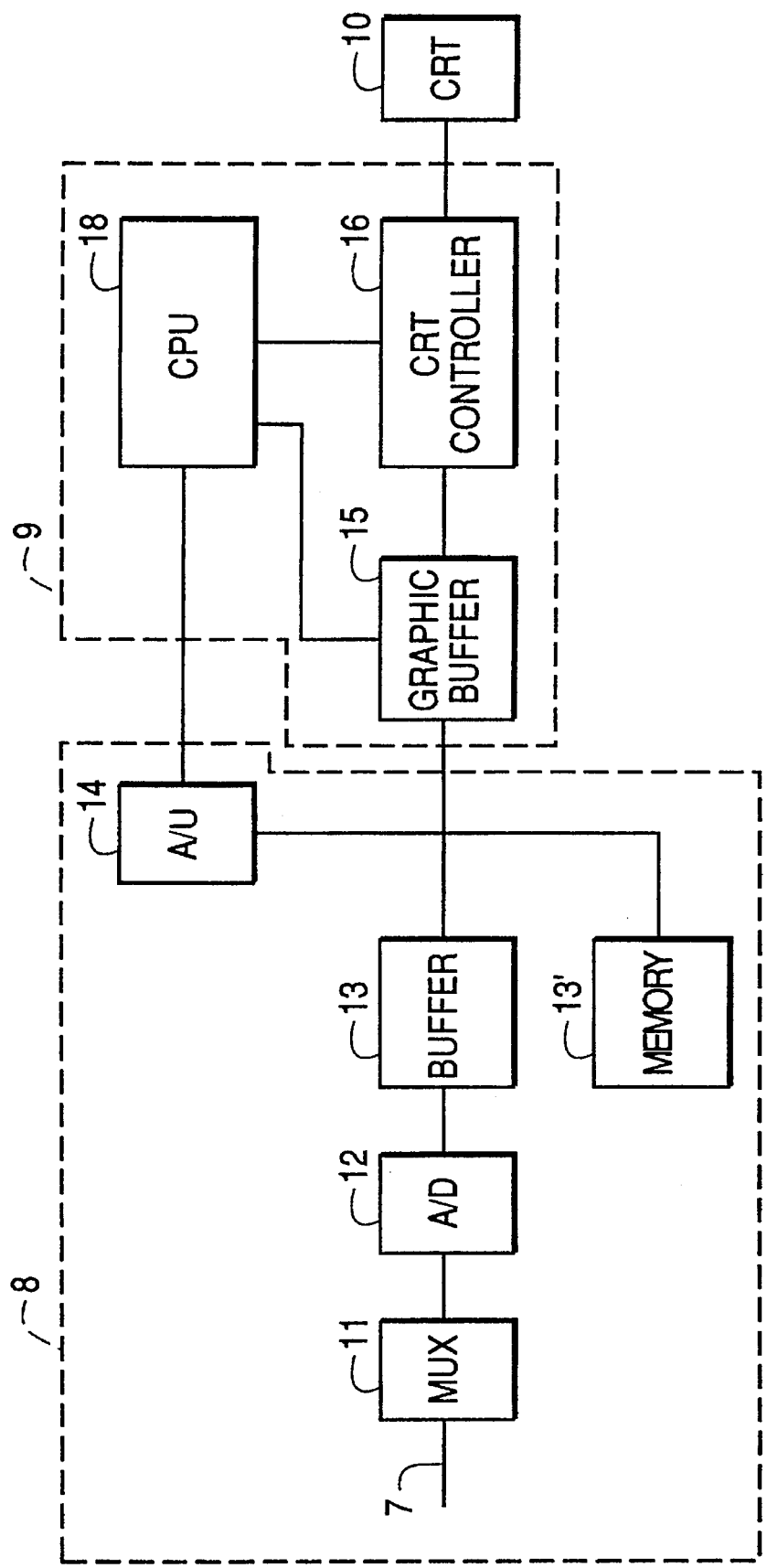
FIG. 3 is a block diagram showing the details of the signal processor 8, the control unit 9 and the display 10 of FIG. 2.

As illustrated by the block diagram of FIG. 3, the proportional electrical signals 7 from the SQUID magnetometers 5 are multiplexed on a time sharing basis by a multiplexer 11. Each signal 7 is then converted to a digital signal by an analog/digital converter 12, and the value of each channel is then applied to a buffer 13. The values for the coefficients of the matrix A (Equation (1)) which are determined by the shape and spacing of the pickup coils 4 and the initial grid point arrangement, are previously stored in a memory 13', and generalized inverse matrix $A^+$ is computed by the normal equations or singular value decomposition of Equations (6) and (8) in an arithmetic unit 14 based on such stored values, with the results being stored in the memory 13'. In the preferred embodiment, the arithmetic unit 14 is a TMS 320-series digital signal processor. One software package which can be used for singular value decomposition is the so-called EISPACK software distributed by National Energy Software Center of Argonne, Ill. and IMSL of Houston, Tex. which performs Equations (6) and (8). The general use of normal equations and singular value decomposition is described in Golub, Golub et al., "Singular Value Decomposition and Least Squares Solutions", Numer. Math, 14, pps. 403–420 (1970), the contents of which are incorporated by reference.

The arithmetic unit 14 converts the estimated current dipole distribution to image data based on the values obtained by inverse estimation from the magnetic measurements, and these data are then stored in a graphics buffer 15 in the control unit 9. A CRT controller 16 then controls operation of the CRT 10 to display the image data. The overall operation of the arithmetic unit 14, graphics buffer 15 and CRT controller 16 is controlled by a master CPU 18. Any standard graphics package can be employed as the control unit 9 in combination with a compatible CRT 10. The CRT 10 in addition to displaying the position of the dipoles is also capable of displaying the amplitude or strength of the dipoles by showing variations in size, color, hue, brightness or three-dimensional illustration.

Figure 4:
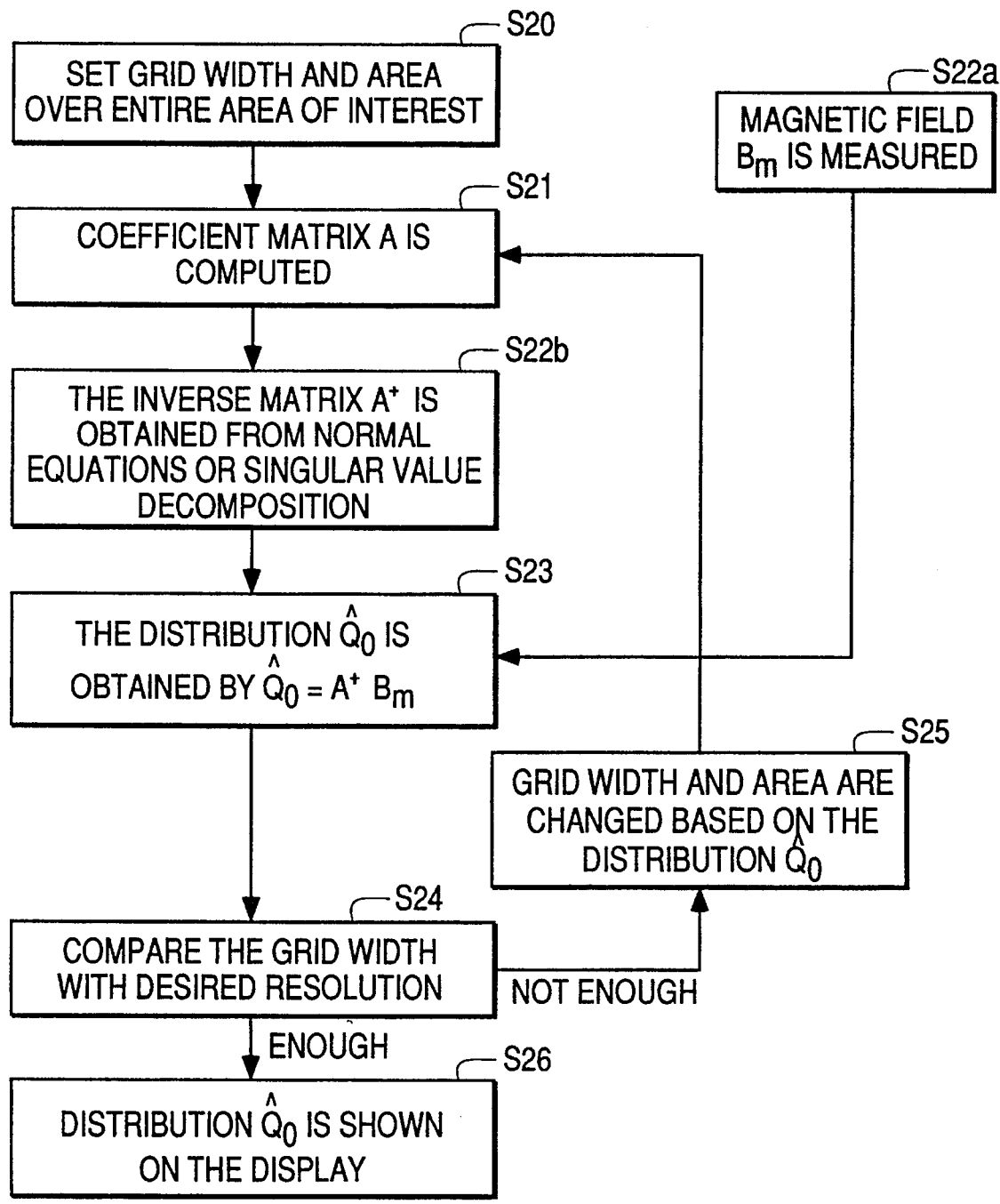
FIG. 4 is a flowchart for describing the operation of the circuitry of FIG. 2.

FIG. 4 is a flowchart for describing the operation of the circuit of FIG. 3, including the inverse estimation algorithm. A grid width and an area for estimation of current dipoles are initialized to cover the region of interest (S20). The coefficient matrix A is computed based on the positions of the pickup coils 4 and dipole grid points (S21). Then, the magnetic field is measured (S22a) and a generalized inverse matrix $A^+$ is obtained from the normal equations or singular value decomposition of Equation (6) and (8) (S22b). An initial estimated distribution $\hat{Q}_0$ is obtained by multiplying magnetic field distribution $B_m$ measured in step S22a by the inverse matrix $A^+$ (S23). If the grid interval or spacing does not reach the desired resolution (S24), then the width and area of the grid are changed (i.e., reduced) based on the initial estimated value $\hat{Q}_0$ (S25). Steps S21–S25 are repeated until the theoretically limited resolution or desired accuracy is obtained. The distribution $\hat{Q}_0$ of the current dipoles finally obtained is displayed on the display unit 10 (S26) to show the position and strength of multiple dipoles.

Figure 5A:
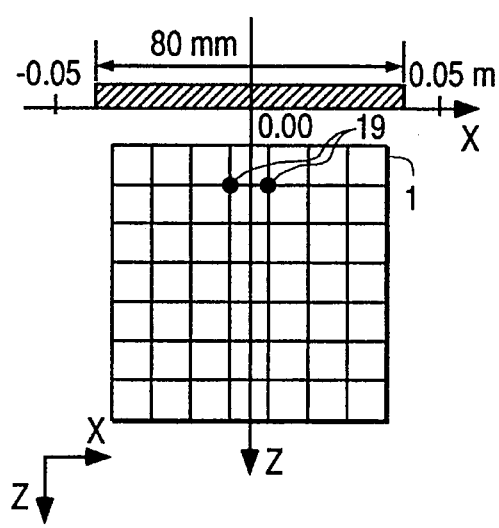
FIGS. 5(a), 5(b) and 5(c) are diagrams of examples for reconstructing a two-dimensional dipole grid in accordance with the present invention.
Figure 5B:
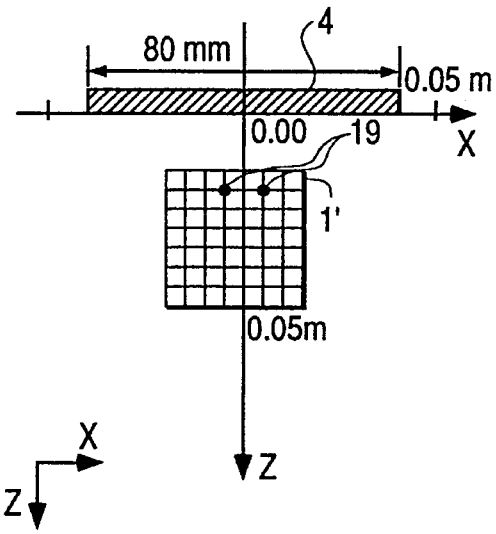
Figure 5C:
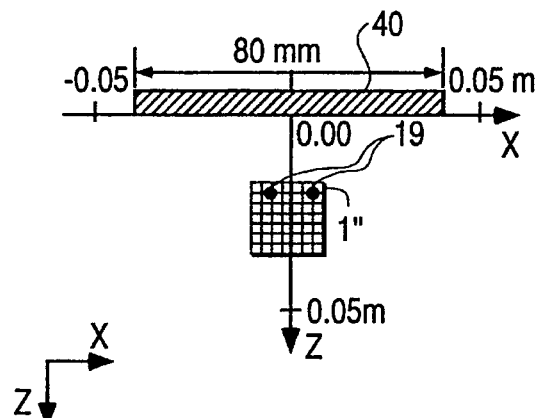
Figure 6A:
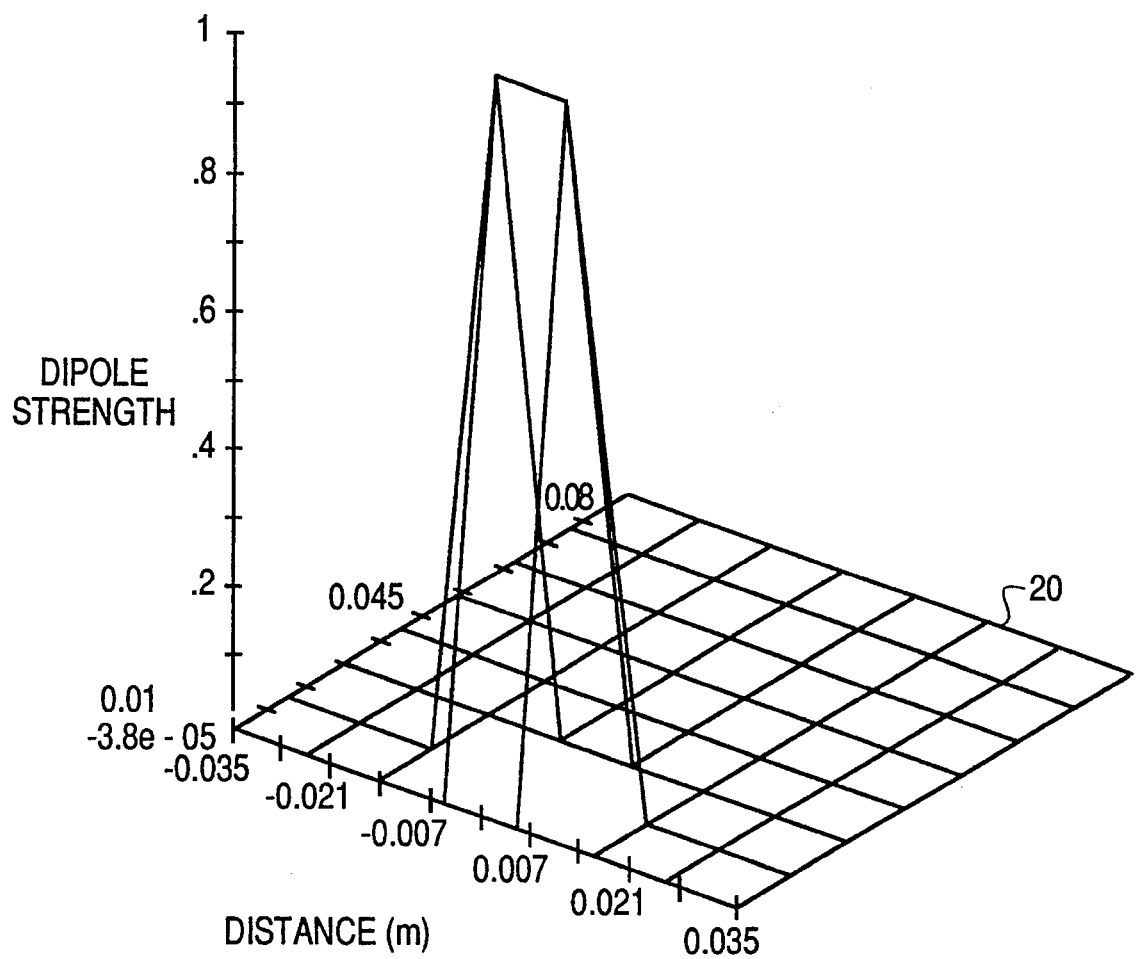
FIGS. 6(a), 6(b) and 6(c) are graphical displays for illustrating the results of the reconstruction of FIGS. 5(a), 5(b) and 5(c), respectively.

FIGS. 5(a), 5(b), 5(c), 6(a), 6(b) and 6(c) illustrate the operation of a preferred embodiment of the present invention where the estimated current dipole grid 1 is set in the form of a plane, and current sources normal to the plane (y-component) are estimated by singular value decomposition. In the case where the sensors or pickup coils 4 are arranged linearly and measure the normal (z-component) of the magnetic field for position estimation for two or more current dipoles 19 on the grid 1 as illustrated in FIG. 5(a), a reconstruction image 20 of a pair of unresolved current dipoles 19 can be obtained as shown in FIG. 6(a) by executing current source position estimation with a rough or coarse setting width for the area where current dipoles may exist. FIG. 6(a) is a graphical display for better visualizing the position and amplitude of the current dipoles 19.

Figure 6B:
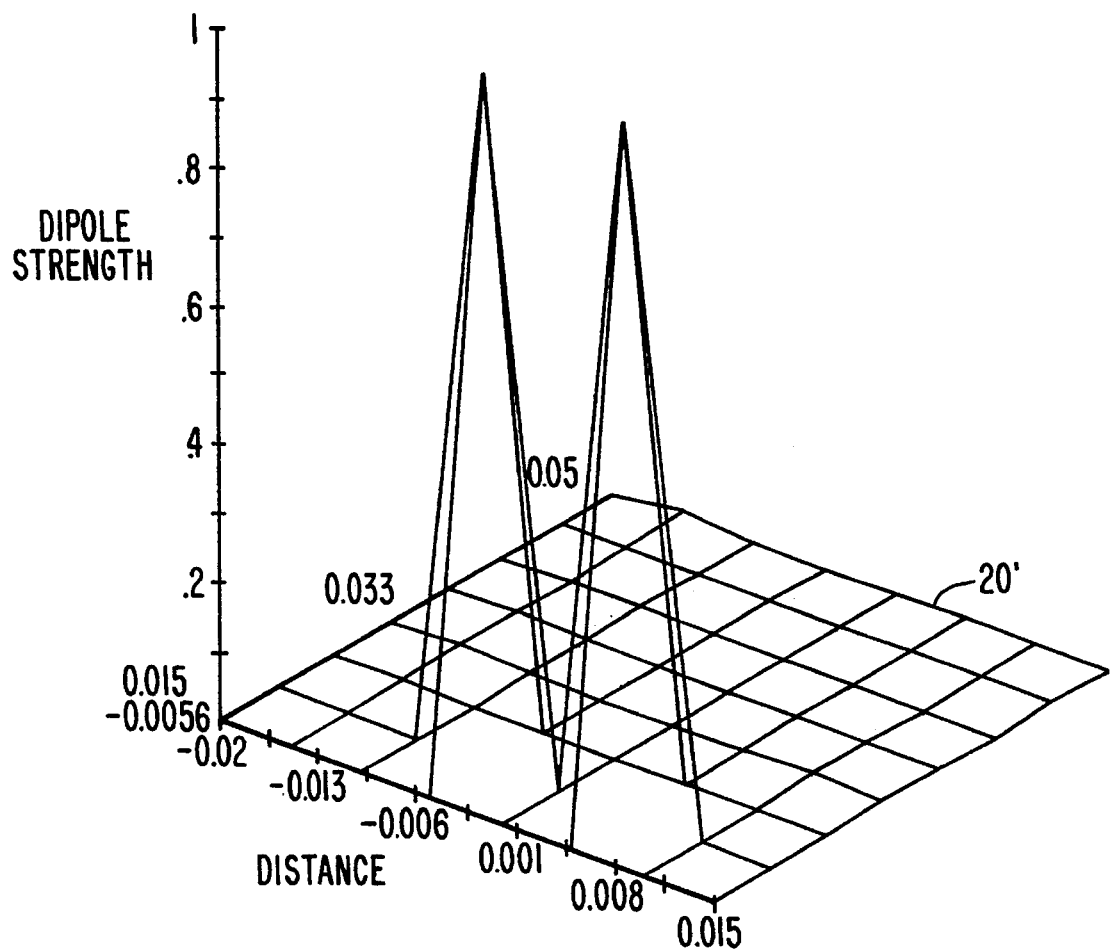
Figure 6C:
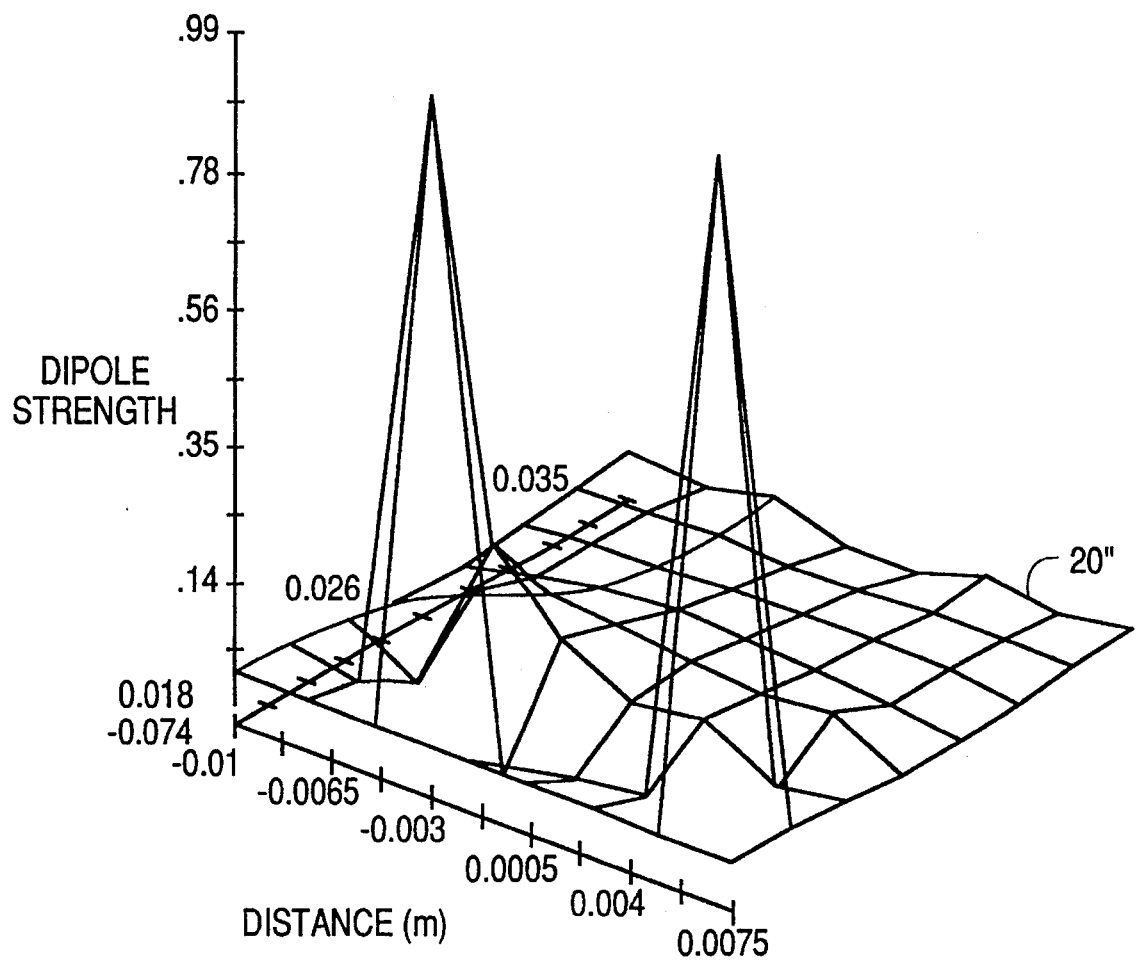

A reconstruction image 20' of two separated current dipoles 19 as shown in FIG. 6(b) can be obtained by estimating, as shown in FIG. 5(b), the current dipole position with a grid 1', having a half-grid width for the measured data. Moreover, as shown in FIG. 5(c), a reconstruction image 20" having twice the resolution can be obtained, as shown in FIG. 6(c), by reducing the width of the current dipole estimation grid to half that shown in FIG. 5(b).

In FIGS. 5(a)–5(c), the x axis in the figure indicates the horizontal direction, while the z axis indicates the vertical direction and the y axis indicates the depth direction into the paper. Moreover, the grid setting interval is reduced in the sequence of 10 mm (FIG. 5(a)), 5 mm (FIG. 5(b)), 2.5 mm (FIG. 5(c)) and positions of the current dipoles 19 are set to (0.005, 0.0, 0.01) and (−0,005, 0.00, 0.01) considering the center position of the sensors 4 as the origin. The sensors 4 are arranged in such a manner that 128 sensors are arranged at equal intervals within a total width of 80 mm. Moreover, the number of current dipole grid points is fixed to 64 points (8×8) although the number can be varied in accordance with the circumstances of a particular use.

Figure 7A:
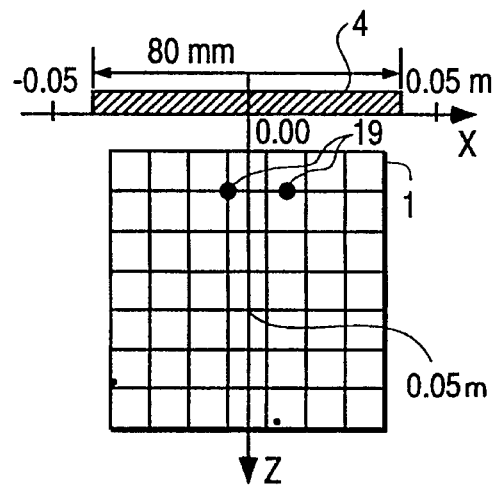
FIGS. 7(a) and 7(b) are diagrams illustrating examples of reconstruction in accordance with the present invention, wherein one of the current dipoles is located between grid points.
Figure 7B:
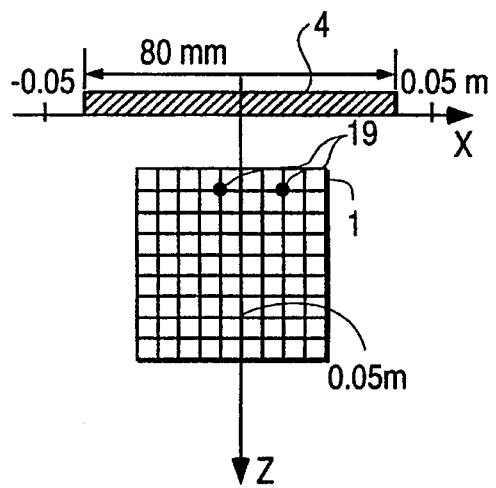
Figure 8A:
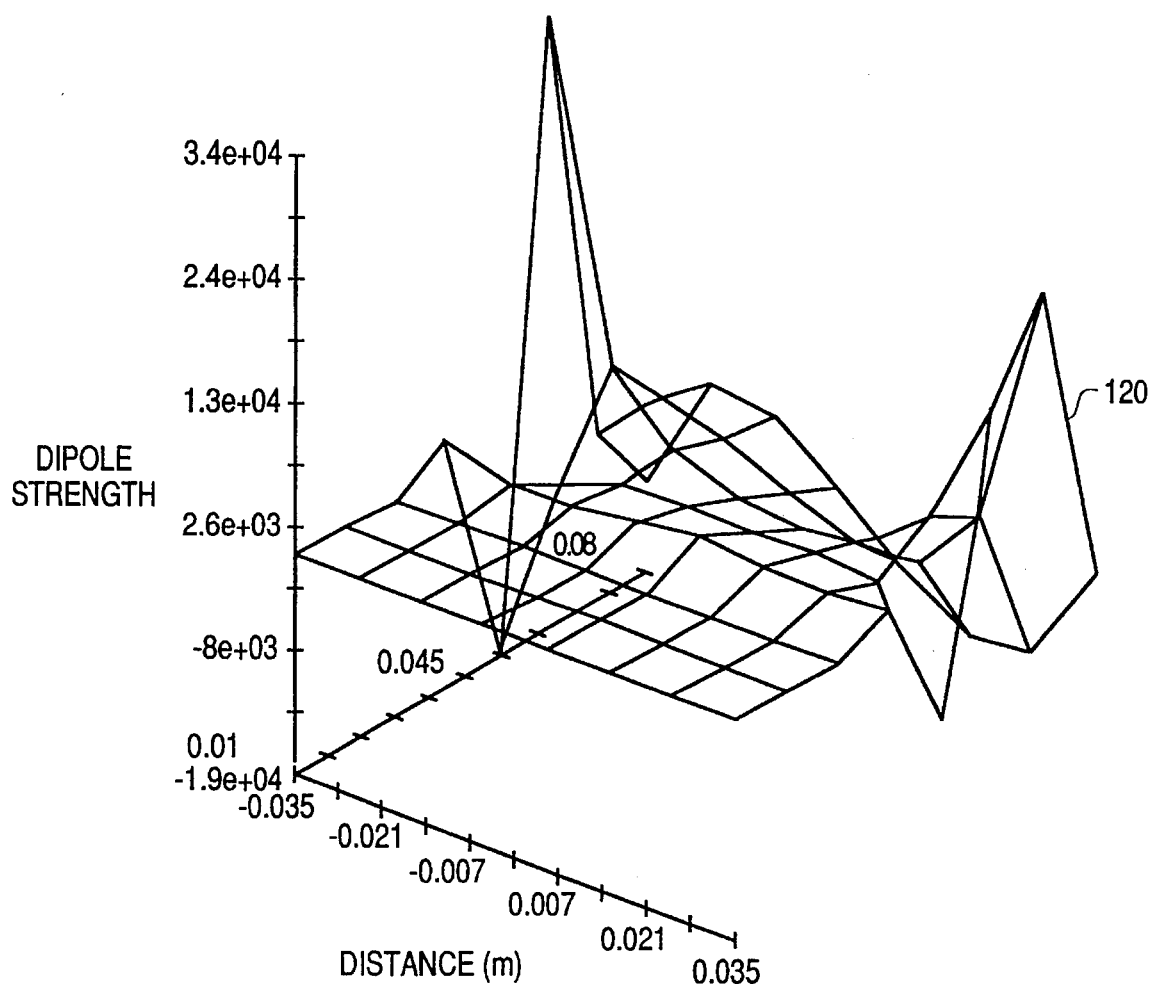
FIGS. 8(a), 8(b) and 8(c) are graphical displays for illustrating the results of reconstruction in accordance with FIGS. 7(a) and 7(b)
Figure 8B:
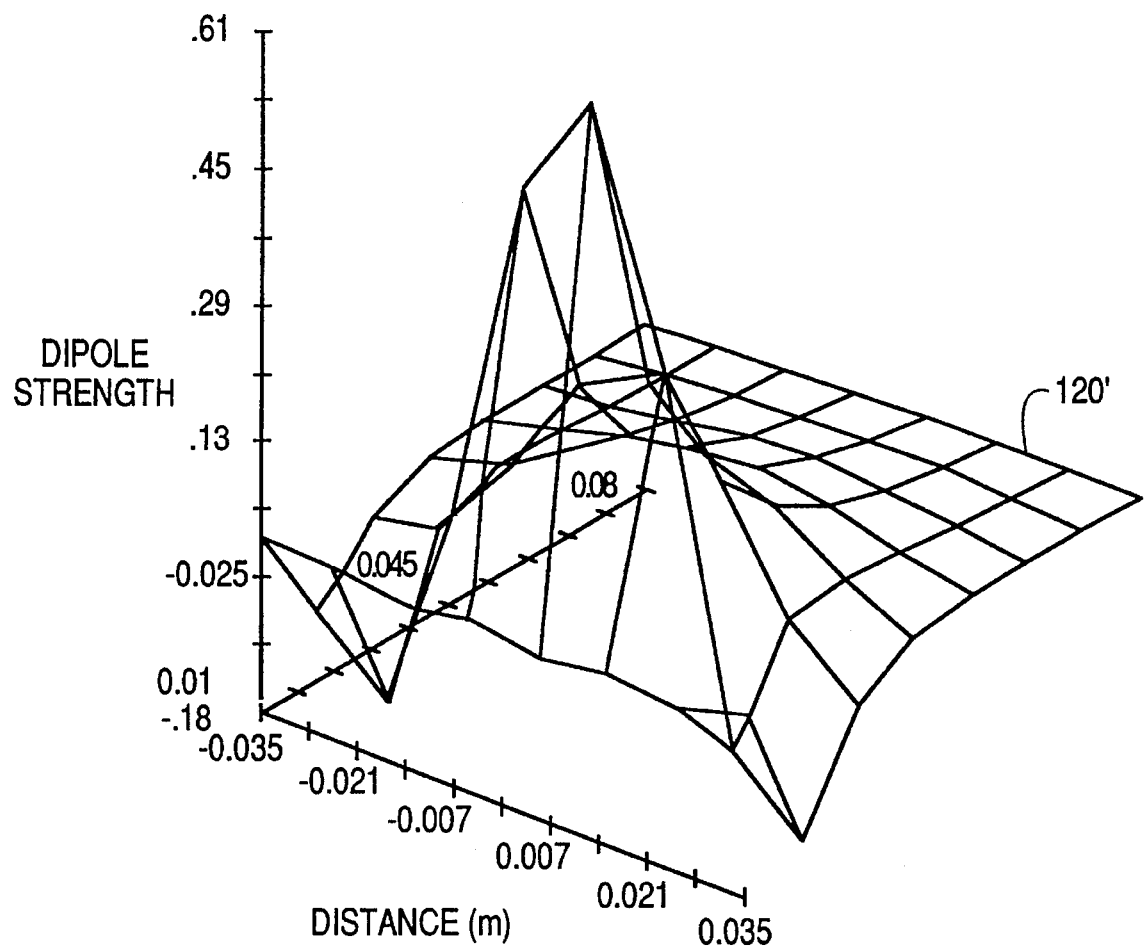
Figure 8C:
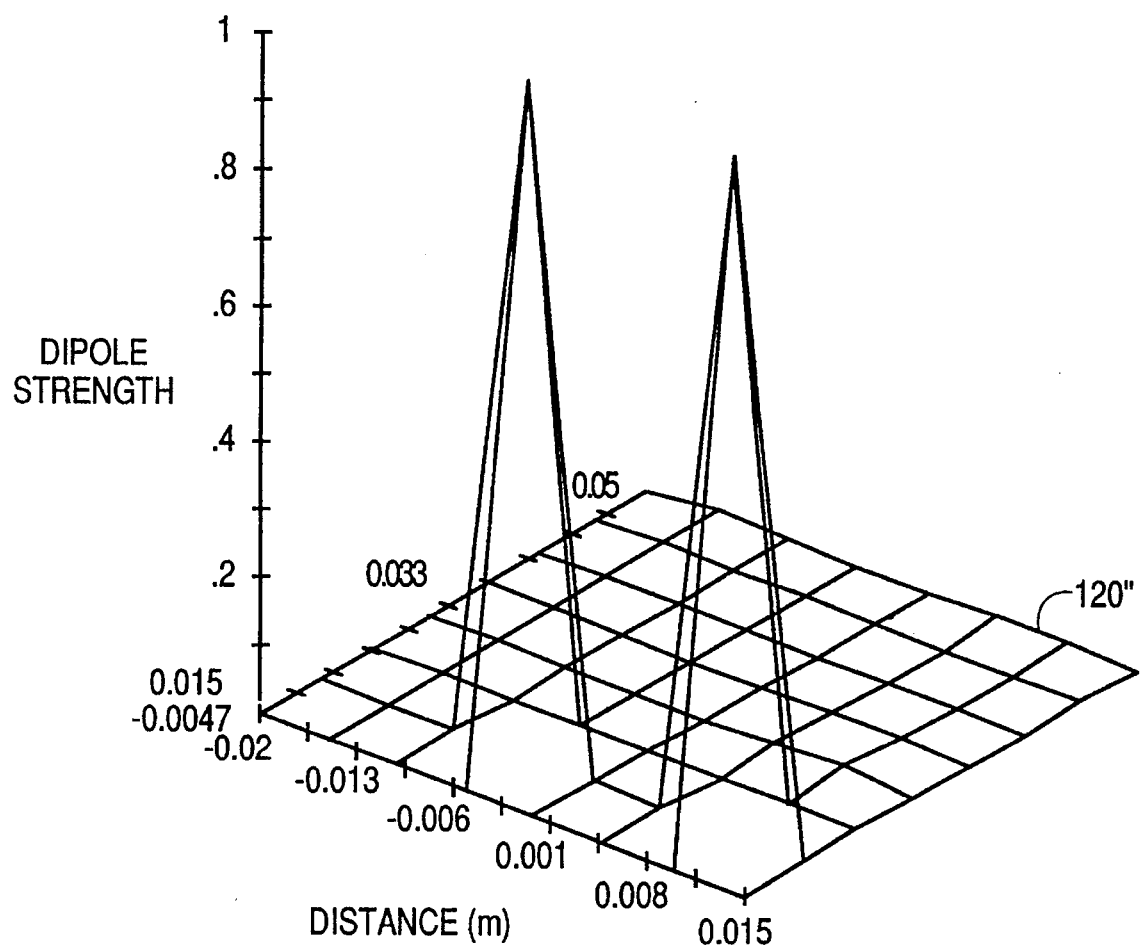

In FIGS. 5(a), 5(b) and 5(c), the current dipoles 19 exist on grid points of the estimated grid 1. However, if a current dipole 19 does not exist on a grid point as shown in FIG. 7(a), and if reconstruction is carried out using all singular values $$\Lambda = (\lambda_1, \lambda_2, \ldots, \lambda_r) \quad (10)$$

up to the rank r of the coefficient matrix A, the influence of the current dipole 19 not existing on the grid becomes large as shown by the graphical display of the reconstruction in FIG. 8(a). This reconstruction contains gross artifacts because the model is not obeyed. Therefore, reconstruction is performed by accumulating the larger singular values sequentially from 1 to K in accordance with the following relation $$\hat{Q} = \sum_{i=1}^{K} v_i \lambda_i^{-1} u_i^T B_m \quad (11)$$

where $v_i$ and $u_i$ are the columns of U and V, respectively, in Equation (8) and $B_m$ is a measured value. As shown in FIG. 8(b), a reconstruction image 120' which is inferior in resolution but more robust with respect to off-grid point sources can be obtained by employing a smaller number of the singular values. The number of singular values used should be sufficient to display a well defined peak in the reconstruction. Moreover, by reducing the grid area as shown in FIG. 7(b), a reconstruction image 120" having a finer resolution grid as shown in FIG. 8(c) can be obtained by reducing the interval of estimation grid 1 in the direction of the observed distribution of the current dipole known from FIG. 8(b). Accordingly, (1) in the initial estimation where the coarse grid 1 (FIG. 7(a)) is employed, a small number of singular values is used for reconstruction to avoid artifacts caused by off-grid dipoles. The probability that a current dipole exists on a grid point is low for coarse grids. The estimation is carried out with coarse resolution under the condition than an element existing outside the grid makes a small contribution to the measured magnetic field and the approximate current dipole position is estimated by the location of the maximum peak in the reconstruction. Then, (2) estimation with higher accuracy can be realized on a smaller grid 1', while the resolution of the estimated current dipole is improved by executing the reconstruction over a smaller sized region. The accumulated number of singular values suitable for a given grid size can be determined by executing the reconstructions while the number of singular values is being increased, until a well-defined peak is observed in the reconstruction. This peak will exist in the vicinity of the current activity and indicates the location about which the next stage of magnification will occur. As the number of magnification steps increases, the artifacts in the reconstruction are due less to model errors (off-grid sources) than to errors in the measured magnetic field. At these latter stages of magnification, the number of singular values is limited by the ratio of signal power to measurement error power. This ratio defines a threshold level. Singular values below the threshold level cannot be used in the reconstruction. The magnification procedure terminates when no further improvement in localization or resolution occurs, which can be identified by noting the number of singular values that are lost in the magnification step. For example, in the planar grid case, if a magnification factor of 2 per linear dimension causes a reduction of four in the number of singular values above the threshold level, no improvement in the magnified reconstruction will be realized. If multiple sources exist, the magnification procedure terminates with the minimum grid area that includes all the multiple sources.

In FIG. 1, the estimated grid of current dipoles is set on a plane. However, the resolution can be improved by reducing the estimated grid of current dipoles in the direction of the active area 2' of a current source, while the position is estimated for a three-dimensional distribution by forming a three-dimensional cubic shape of the estimated grid 100 of current dipoles as shown in FIGS. 9(a) and 9(b).

In addition, in the case of setting the estimation points for the current source, it is not necessary to include grid points where current sources cannot exist. Instead, the grid may be set in accordance with the shape of the estimated area. For instance, in the case of a circular material, the estimation points can be set on a polar coordinate grid 101 as shown in FIG. 10(a). In the case of a brain, information more useful for diagnosis can be obtained by determining a grid 102 having grid points in accordance with the shape of the periphery of the brain as shown in FIG. 10(b). In the case of the heart, a solution exhibiting a smaller error can be obtained by setting a grid 103 having grid points so as to avoid the region of the heart where a conductive system does not exist, such as an atrium or ventricle, as shown in FIG. 10(c). Thus, as used in this application, the term grid refers to any defined set of grid points in a region (two-dimensional or three-dimensional). In order to implement the specifically shaped grids such as grids 102 and 103, magnetic resonance imaging (MRI), diagnostic ultrasound imaging (US) or X-ray computed tomography (X-RAY CT) can be used to determine the specific grid points which are most suitable for achieving high accuracy. Further, depending on the grid arrangement selected, it can be desirable to position the sensors 4 in a non-linear arrangement such as an arc or circle.

Figure 11:
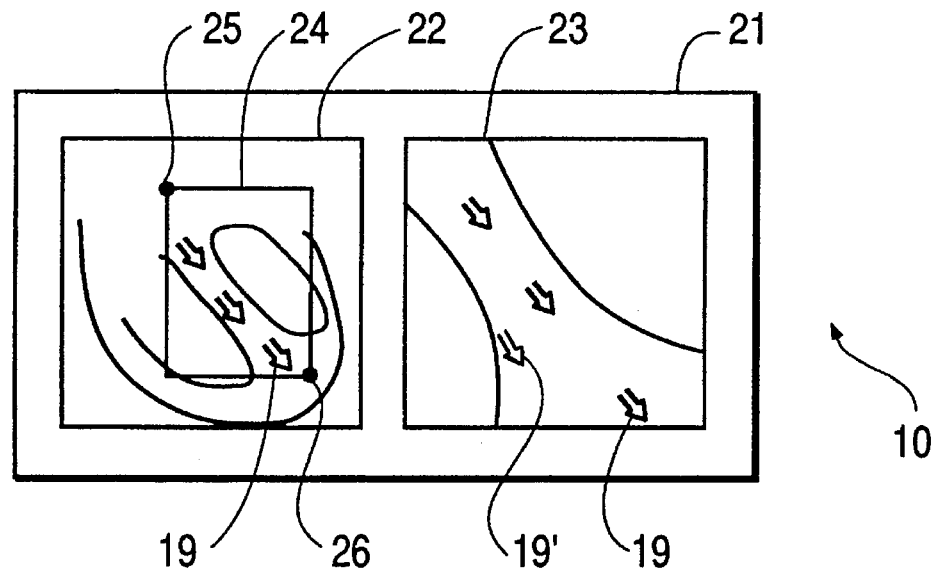
FIG. 11 is a diagram for illustrating a display device having two display screens in accordance with the present invention.

There are a number of ways for displaying the results of biomagnetic imaging for diagnostic purposes in accordance with the present invention. For example, FIG. 11 illustrates that the display 10 formed by a display device 21 having first and second display screens 22 and 23 for displaying a non-magnified image and a magnified image of the current dipoles obtained by the inverse estimation. Based on the inverse estimation, a desired area 24 on screen 22 can be selected for display in a magnified state on screen 23. The desired area 24 can be selected by designating corner points 25 and 26 on screen 23 by using an operator input device such as a keyboard or a mouse. The screens 22 and 23 can be used for diagnostic purposes to view the position and strength of the current dipoles. The sample display of FIG. 11 is that of a portion of a heart and illustrates current dipoles 19 in the center wall of the heart. Based on this display, it is possible for a physician to determine whether electrical activity in the heart is normal. For example, if the resolution of the selected area 24 of screen 22 is increased, a physician might be able to better see a dipole 19' located along the edge of the center wall of the heart, which may indicate a malfunction in the heart.

Figure 12:
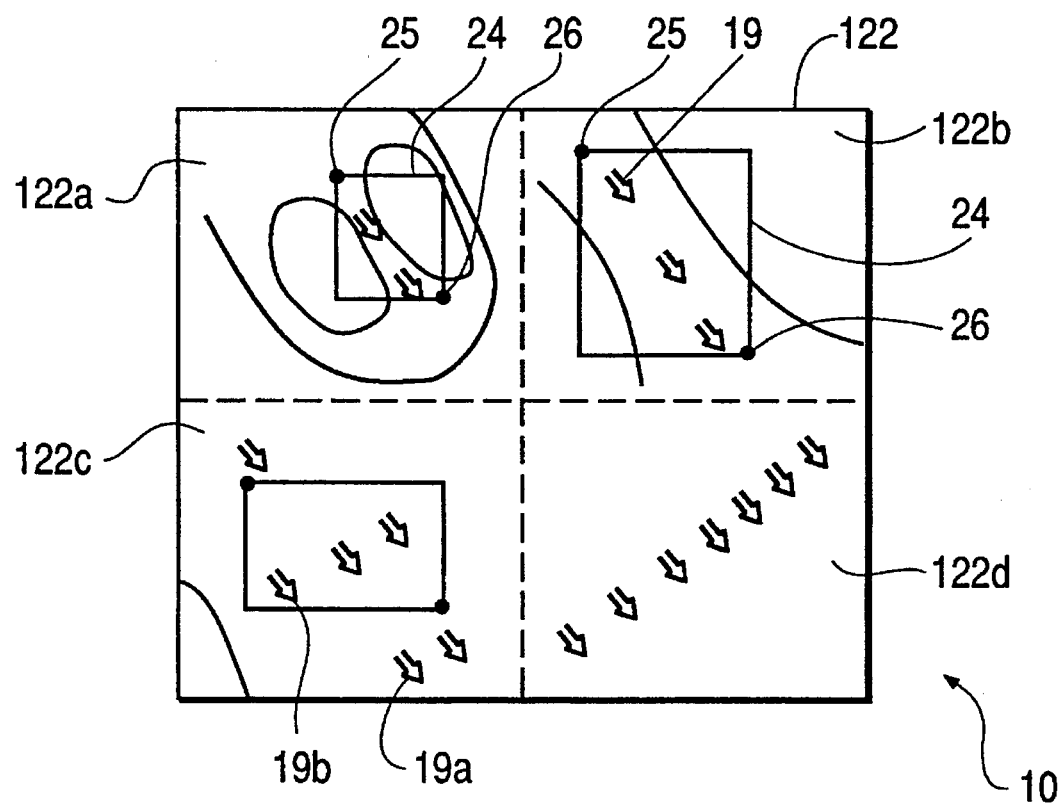
FIG. 12 is a diagram illustrating a display device having four separate display areas with different levels of resolution on a single screen.

In an alternate display mode in accordance with the present invention, a single display 122 is divided or split into a plurality of display areas as shown in FIG. 12. The divided areas are designated sequentially as 122a, 122b, 122c and 122d and are capable of realizing successively magnified displays. Moreover, if a current dipole 19a exists outside the selected area as indicated in display area 122c, a current dipole 19b within the frame can be estimated under the condition that the current dipole 19a existing outside the selected area provides a smaller influence. In particular, the magnetic field $B_{out}$, terminated by a current dipole in the region outside the frame can be computed using the Biot-Savart law as preprocessing for the next inverse estimation. Then inverse estimation is executed using the following equation for subtracting the outside magnetic field from the measured magnetic field $B_m$:

$$B_{in} = B_m - B_{out} \tag{12}$$

and $B_{in}$ is then used in the inverse estimation.

Figure 13:
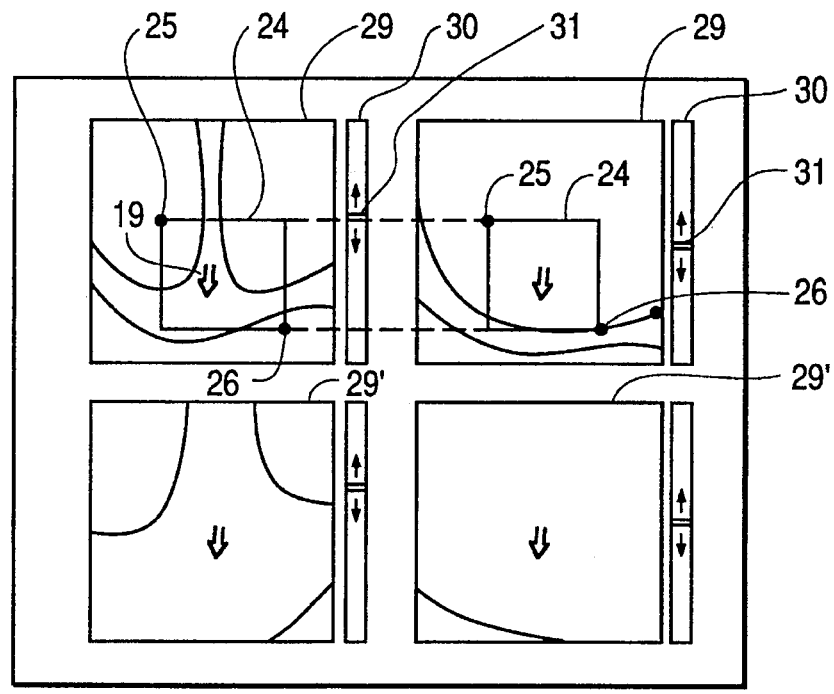
FIG. 13 is a diagram for illustrating a display having multiple display screens for displaying different planes of a subject to be imaged and having the capability of selecting the depth of the plane being displayed.
Figure 14:
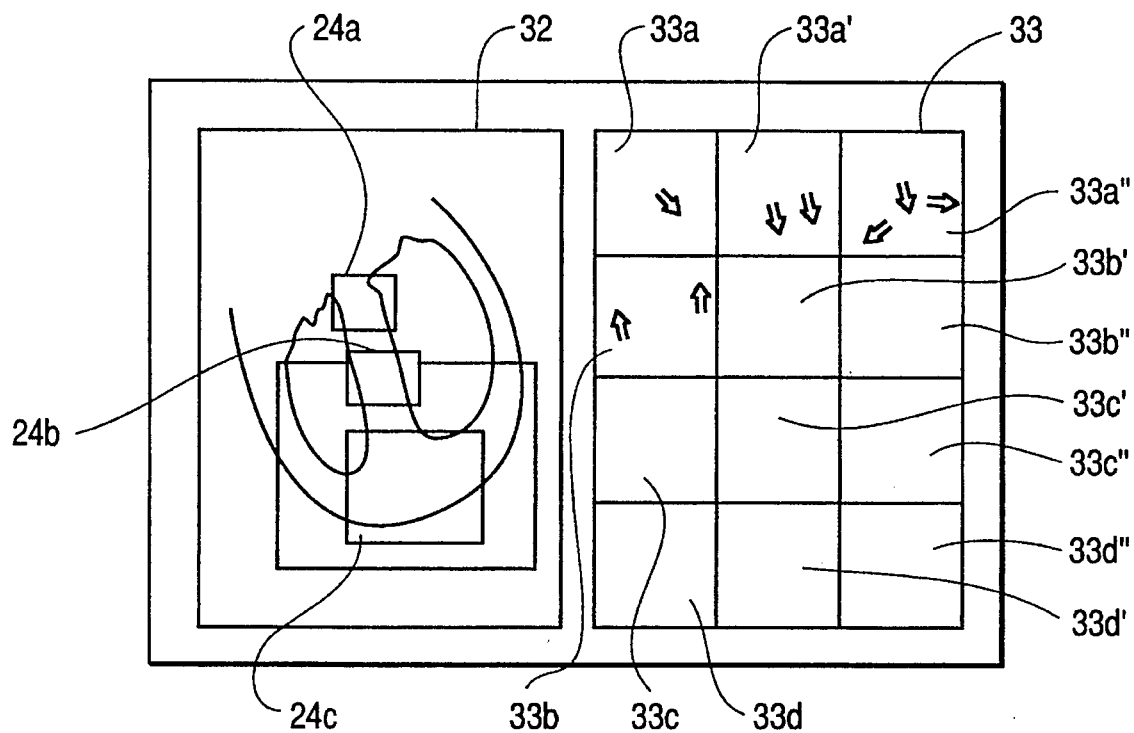
FIG. 14 is a diagram for illustrating a display having a primary screen and having a secondary screen for selectively displaying a plurality of portions of the primary screen at different times, in order to simulate movement of the current dipoles within the subject.

Moreover, in the case of estimating a three-dimensional current dipole distribution, planar sections which are mutually vertical with respect to each other can be displayed on adjacent screens 29 as shown in FIG. 13. Further, a desired cross-section within the three-dimensional distribution can be constructed by providing an indicator bar 31 which can be changed in height within a rectangle 30 in accordance with the depth position of the selected plane for display at a desired three-dimensional section. Further, estimation suitable for diagnosis can be realized by designating a desired area using frame 24 (described above with respect to FIG. 12) within the screens 29 and reconstruction will be executed to produce magnified displays on lower screens 29'.

If it is desired to display different magnified results over time for different selected areas 24, then the CRT 10 can be divided into screens 32 and 33, wherein screen 32 displays a tomographic image provided by X-ray, ultrasound or an MRI image of a subject and different frames 24a, 24b, 24c and 24d are identified for magnified viewing to show the location of the reconstruction grid on the MRI or tomographic image. No dipoles are displayed on screen 32. Instead, dipole display areas 33a–33d correspond to frames 24a–24d, respectively and are displayed at a first time $t_1$. Then, at a designated time $t_2$ (e.g., 10 seconds after $t_1$), a new set of display areas 33a'–33d' is generated, followed by an additional set of displays at a time $t_3$ in display areas 33a'–33d'. This type of display can be used to better detect changes in the strength or position of current sources or dipoles over time.

In accordance with another aspect of the present invention, images produced by magnetic resonance imaging (MRI) and biomagnetic imaging (BMI or MSI) can be superimposed as a diagnostic tool. In this aspect, image data showing major contours or features of an MRI image are selected and biomagnetic imaging data generated in the manner described above, is employed to generate an image which is superimposed on the selected portion on the MRI image.

Figure 15:
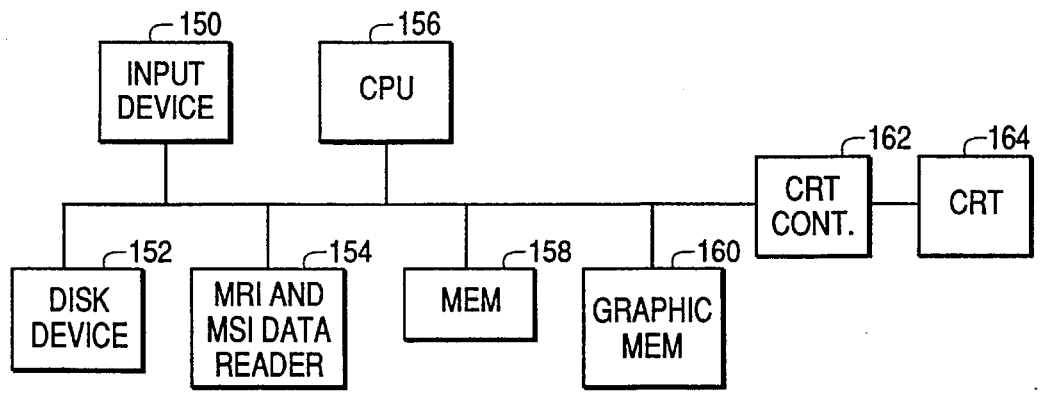
FIG. 15 is a block diagram for illustrating a system for superimposing an MRI image and a biomagnetic or MSI image on a single CRT in accordance with the present invention.

FIG. 15 is a block diagram of an embodiment of an image superposition system which can be used to superimpose MSI and MRI images. Referring to FIG. 15, an input device 150 such as a mouse is used to select a portion of an image which is to be displayed at a magnified level (i.e., similar to area 24 in FIG. 11). A hard disk 152 stores data input via the input device. An MRI and MSI data reader 154 is used to read graphic data from an MRI, as well as MSI data which is output, for example, from the signal processor 8 of FIG. 2. The data reader 154 may be part of a local area network or may be another kind of data input device, such as a tape reader. A central processing unit 156 controls the operations of the image superposition system of FIG. 15. A memory 158 stores a program for implementing the image superposition operation. A graphic memory 160 stores the MRI data and the MSI data. A CRT controller 162 receives the graphic data which has been processed by the CPU 156 and provides data for a superimposed display on a CRT 164. Thus, by employing the system of FIG. 15, overlapping displays of an MRI image and a current source image produce by biomagnetic imaging can be shown on a single display. Further, portions of the display can be selected for higher resolution in the manner described above with respect to FIGS. 11–14. In the preferred embodiment, the system of FIG. 15 is a computer-based system capable of operating a multiple window system software package such as the X WINDOW software produced by MIT.

Figure 16:
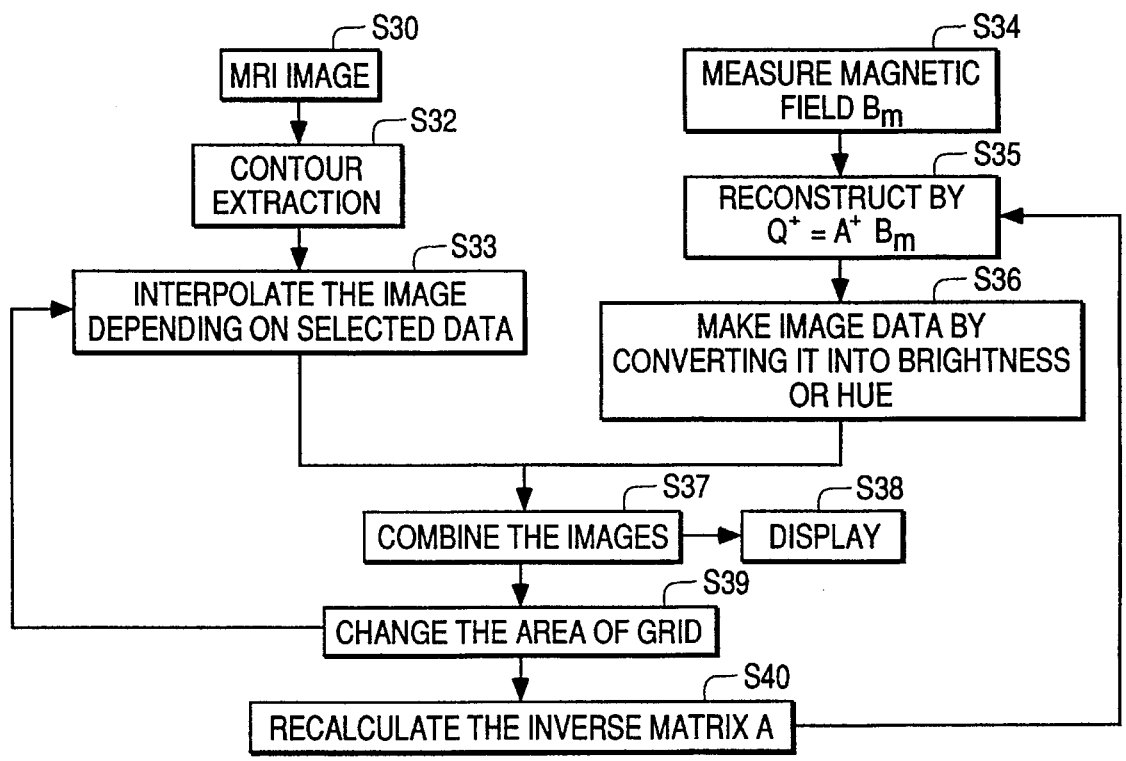
FIG. 16 is a flowchart for describing the operation of the circuit of FIG. 15 in accordance with the present invention.

FIG. 16 is a flowchart illustrating the operation of the system of FIG. 15. Referring to FIG. 16, MRI image data is first read (S30) and contour extraction is carried out to select a contour from the MRI image based on a concentration threshold value (S32). This allows only major contours or features of the MRI image to be selected for display. Next, image interpolation is performed to fill in or interpolate between the extracted data points depending on the selected area formed based on such data (S33). This image interpolation is similar to that used in ultrasonic diagnostics to fill in data for selected areas. Next, the magnetic field of the subject is measured (S34) and reconstruction is performed to produce image data for displaying the positions of current sources by inverse estimation based on the measured magnetic field data $B_m$ (S35). MSI image data is generated to illustrate intensity based on brightness or hue (S36). The MSI image data obtained in S36 and the MRI image data obtained in S33 are combined (S37) and are displayed on the display 164 (S38). Thus, an overlapping image combining an MRI image and an estimated current dipole or MSI image can be displayed concurrently. Further, if higher resolution is desired, the area of the grid can be changed (S39) and the inverse matrix A recalculated (S40) so as to produce a new display of higher resolution. It should be noted that when the grid area is changed, it is required to again interpolate the image based on the extracted data for the MRI image (S33).

Figure 17:
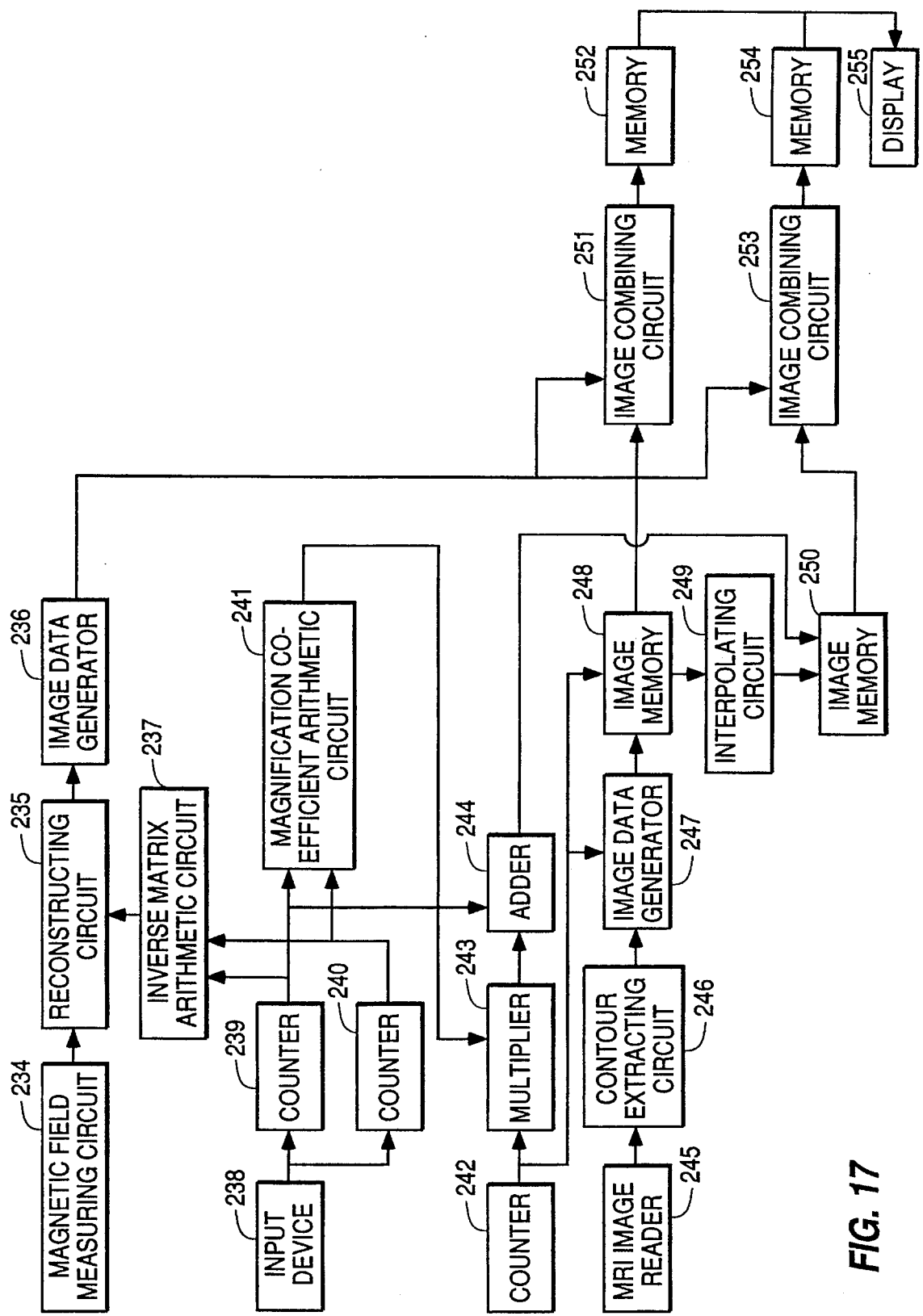
FIG. 17 is a block diagram of an alternative system for superimposing an MSI image on an MRI image which is a hardware version corresponding to the circuit of FIG. 15.
Figure 18:
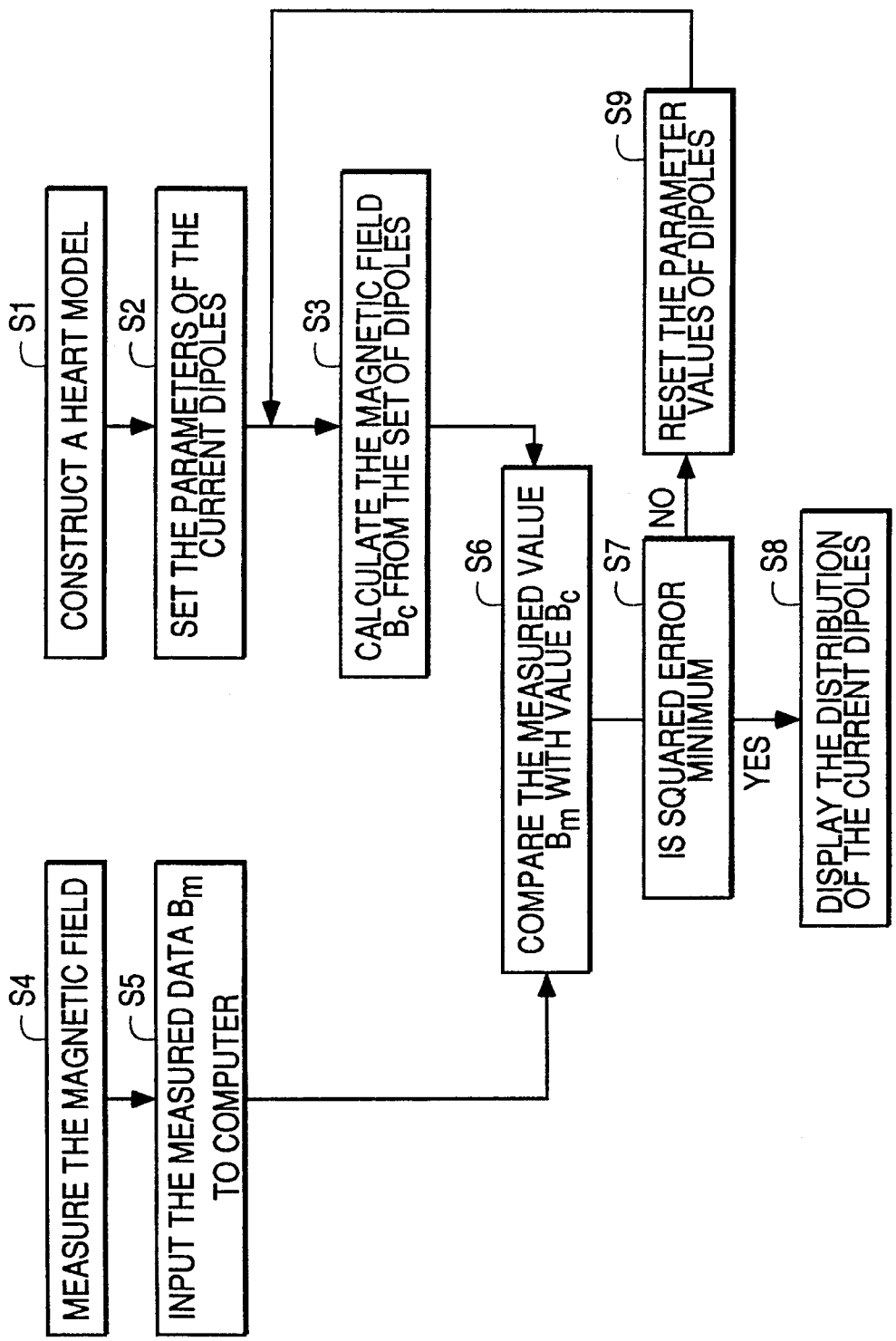
FIG. 18 is a flowchart for describing the operation of a prior art biomagnetic display device.

FIG. 17 is an alternative hardware embodiment for achieving the processing illustrated in FIG. 16. Referring to FIG. 17, a magnetic field measuring circuit 234 provides measured data which is converted to a current dipole density distribution by an inverse estimation circuit or reconstructing circuit 235. An image data generating circuits 236 converts the current dipole density distribution to a contrast image which is provided to image combining circuits 251 and 253. Meanwhile, the coordinates (x1, y1), (x2, y2) of a magnified area or frame (similar to frame 24) are obtained from counters 239 and 240 which are synchronized with the position of a cursor on the image controlled by an input device 238, such as a mouse. The outputs of the counters 239 and 240 are provided to an inverse matrix arithmetic circuit 237 which controls the reconstructing circuit 235, and to a magnification coefficient arithmetic circuit 241 which provides a magnification coefficient "a" to a multiplier 243. An MRI image reader 245 provides MRI image data to a contour extracting circuit 246 which extracts selected MRI image data and provides the selected MRI image data to an image data generator 247. A counter 242 is used to generate an address to be used for image interpolation and to address an image memory 248. In addition, counter 242 provides an output to control the output of image data generator 247. The counter 242 also provides an output to a multiplier 243 which multiplies the magnification coefficient "a" by the value of counter 242 to provide an offset value to an adder 244. The output of the adder 244 is used to address the image memory 250 to identify the address of the magnified image in the image memory 250. The addressed image data of image memory 248 is sent to an image memory 250 via an interpolating circuit 249 in which a vacant image data area generated by magnification is filled in with interpolation data generated by the interpolation circuit 249. The extraction of contour data by contour extracting circuit 246 before the MRI image data enters the image memory 248 is performed in order to clarify the difference of images between respective tissues and images depending on the combination of contrast changes in the current dipole. A magnified image stored in the image memory 250 and non-magnified image data from image memory 248 are sent to the image combining circuits 251 and 253 in order to generate image data which indicates the distribution of the MRI image at the time of magnification. This image data is combined with the image data provided by the image data generator 236 in the image combining circuits 251 and 253 and the combined images are stored in the image or graphic memories 252 and 254 and are simultaneously displayed on the screen of a display 255. Thus, the current dipole can be estimated while the desired area is magnified.

To illustrate the operation of the subject invention, simulations were conducted using an 8×8 grid (128 unknowns) situated perpendicular to a square planar array of 256 sensors measuring the Z-component of the magnetic field. Simulations were performed by using either a single randomly-placed dipole, to test for location accuracy, or a pair of dipoles having random location, spacing and orientation to investigate the resolution capabilities of the procedure. Magnetic measurements were computed by using the Biot-Savart Law and a random number was added to the measurements to simulate the effects of a given signal-to-noise ratio. In cases where a region of activity was observed within the reconstruction region, the 64 element grid area was reduced to 25%, that is, a 50% reduction in each dimension and shifted so that the maximum of the observed reconstruction fell near the center of the reduced grid area. The reconstruction was then repeated using the new grid points. The procedure terminated when no further improvement in resolution was achieved. The single dipole results using both simulated and real data were compared with the dipole localization procedure using the Marquardt algorithm described by Reklaitis et al., Engineering Optimization, Methods and Applications, John Wiley & Sons, New York (1983), the contents of which are incorporated by reference.

In the in vitro dipole experiments, a single dipole 2 cm long, was constructed and driven with a peak current of 50 mA, to produce $Q=10^{-3}$ A-m. The single dipole was placed at various locations in a saline solution within a cubic container. The magnetic field flux normal to the surface of the container was measured with a one centimeter diameter coil having 100 turns, which was translated to simulate a 15×15 sensor array (225 sensors). The coil was attached to a preamplifier feeding a Biomation 8100 A/D converter. Different noise levels in the measurements were obtained by averaging the appropriate number of signals over time. These measurements were applied to the same program used in the simulations. The sensitivities of this approach are described in terms of the signal-to-noise ratio in the measurements and the depth of the dipole(s) below the sensor plane. The single dipole results using the system of the present invention were comparable to those obtained using the Marquardt algorithm. As the depth of the dipole increased or the SNR decreased, the localization accuracy decreased.

As explained previously, according to the present invention, the position of current sources can be estimated with high accuracy using a smaller number of pickup coils from the magnetic field generated in a living body. Moreover, the "zoom" technique of the present invention allows a desired area to be zoomed in on, and magnified on the display screen. Therefore, the present invention is useful for estimating the positions of regions diseased by brain malfunction, myocardial infarction or irregular pulse and provides a significant improvement in the field of biomedical magnetism measuring apparatus. Further, the method and apparatus of the present invention have applicability to any field in which it is desired to generate an image of current sources within a particular living body, subject or material.

The foregoing describes the preferred embodiments of the present invention and is considered illustrative of the principles of the present invention. Further, since numerous modifications and changes will readily occur to those skilled in the art, it is not desired to limit the invention to the exact construction and applications shown and described, and accordingly, all suitable modifications and equivalents may be resorted to, falling within the scope of the invention in the appended claims and their equivalents.

What is claimed is:

1. A method of displaying medical imaging data, comprising the steps of:
    (a) providing biomedical magnetism image data;
    (b) providing medical image data other than biomedical magnetism image data;
    (c) selecting contour image data from the medical image data; and
    (d) generating a display by superimposing the biomedical magnetism image on the selected contour image.

2. A method as set forth in claim 1, wherein said step (b) comprises providing MRI image data.

3. A method as set forth in claim 1, wherein said step (a) comprises substeps of:
    (a1) defining a grid having a first region and having multiple grid points;
    (a2) measuring a magnetic field generated by current sources located within a portion of a subject corresponding to the defined grid;
    (a3) determining a distribution of current sources on the defined grid based on the measured magnetic fields; and
    (a4) modifying the defined grid to have a second region which is smaller than the first region to increase the resolution of the current sources distributed on the grid.

4. A method as set forth in claim 3, wherein said substep (a3) comprises performing singular value decomposition using selected singular values.

* * * * *